US012491340B2

(12) United States Patent
Enerson et al.

(10) Patent No.: US 12,491,340 B2
(45) Date of Patent: Dec. 9, 2025

(54) GUIDING SHEATH WITH PRESSURE RELIEF CHANNEL

(71) Applicant: Oscor Inc., Palm Harbor, FL (US)

(72) Inventors: Andrew J. Enerson, New Port Richey, FL (US); Thomas Gabriel Osypka, Palm Harbor, FL (US)

(73) Assignee: Greatbatch Ltd., Clarence, NY (US)

( * ) Notice: Subject to any disclaimer, the term of this patent is extended or adjusted under 35 U.S.C. 154(b) by 928 days.

(21) Appl. No.: 17/472,100

(22) Filed: Sep. 10, 2021

(65) Prior Publication Data

US 2022/0080155 A1 Mar. 17, 2022

Related U.S. Application Data

(60) Provisional application No. 63/077,337, filed on Sep. 11, 2020.

(51) Int. Cl.
*A61M 25/01* (2006.01)
*A61M 25/00* (2006.01)

(52) U.S. Cl.
CPC ...... *A61M 25/0147* (2013.01); *A61M 25/005* (2013.01); *A61M 2025/0047* (2013.01)

(58) Field of Classification Search
CPC ........ A61M 2025/0047; A61M 25/147; A61M 25/005; A61M 25/00; A61M 25/0009; A61M 25/0012; A61M 25/0013; A61M 25/0021; A61M 25/0023; A61M 25/0028; A61M 25/0029; A61M 25/003; A61M 25/0032; A61M 25/0043; A61M 25/0133; A61M 25/0147
USPC ...................................... 604/95.04, 528, 523
See application file for complete search history.

(56) References Cited

U.S. PATENT DOCUMENTS 5,221,270 A * 6/1993 Parker ................ A61M 25/005 604/523
5,876,385 A * 3/1999 Ikari ................ A61M 25/0041 604/523
6,533,770 B1 * 3/2003 Lepulu ............. A61M 25/0012 604/524
6,689,120 B1 * 2/2004 Gerdts ................ A61M 25/005 604/526
6,761,172 B2 * 7/2004 Boussignac ........... A61M 16/12 128/207.14
9,572,957 B2 * 2/2017 Osypka ............. A61M 25/0136
10,058,668 B2 * 8/2018 Wondka ............ A61M 16/0434
2005/0222585 A1 * 10/2005 Miyata .............. A61M 25/0068 606/127
2007/0250150 A1 * 10/2007 Pal ........................ A61F 2/2436 606/108
2008/0183103 A1 * 7/2008 Blankenship ..... A61M 25/0068 600/585
2008/0262430 A1 * 10/2008 Anderson ............. A61M 25/09 604/165.01

(Continued)

*Primary Examiner* — James D Ponton
(74) *Attorney, Agent, or Firm* — Michael F. Scalise

(57) ABSTRACT

A medical device including an elongated tubular body having opposed proximal and distal end portions and defining a longitudinal axis, the elongated tubular body including an interior lumen extending therethrough, wherein an inner surface of the interior lumen includes at least one longitudinal depression formed therein, configured to provide pressure relief to accommodate movement of a medical device passing through the interior lumen.

17 Claims, 2 Drawing Sheets

(56) References Cited

U.S. PATENT DOCUMENTS

| | | | | |
|---|---|---|---|---|
| 2009/0312827 | A1* | 12/2009 | Stapleton | A61M 25/104 604/103.1 |
| 2010/0094257 | A1* | 4/2010 | Stalker | A61M 25/01 604/524 |
| 2016/0175563 | A1* | 6/2016 | Woehr | A61M 25/0606 604/168.01 |
| 2017/0128703 | A1* | 5/2017 | Elgaard Pederson | A61M 25/1002 |
| 2018/0207395 | A1* | 7/2018 | Bulman | A61F 2/95 |
| 2018/0339130 | A1* | 11/2018 | Ogle | A61M 25/0069 |
| 2019/0054270 | A1* | 2/2019 | Bornhoft | A61M 25/0032 |

* cited by examiner

GUIDING SHEATH WITH PRESSURE RELIEF CHANNEL

CROSS-REFERENCE TO RELATED APPLICATION

The subject application claims the benefit of priority to U.S. Provisional Patent Application Ser. No. 63/077,337, which was filed on Sep. 11, 2020, the contents of which are incorporated by reference herein in its entirety.

BACKGROUND OF THE INVENTION

1. Field of the Invention

The subject invention is directed to an introducer or guiding sheath catheter, and more particularly, to an introducer or guiding sheath catheter for delivering a device, such as a balloon catheter, stent, or other device.

2. Description of Related Art

Introducer systems and guiding sheaths are commonly used to introduce and guide medical devices and applications to a desired location inside the human vascular system. These devices commonly have a concentric round through-lumen, with a tapered distal tip for easy insertion into the vascular system, and a proximal end with a hemostatic valve, allowing the user to introduce other devices into the sheath from the proximal side through a hemostatic valve. The system typically includes sheaths to deliver other medical devices, such as stents or artificial aortic valves, or therapies such as electrophysiology catheters, balloon catheters, or other applications to the desired treatment location inside the heart or vascular system. Often such devices are complex in shape and expand throughout the inner lumen, and the complete inner diameter of the sheath, possibly resulting in a suction effect, making it difficult to move the device inside the sheath diameter.

The traditional systems and methods have been considered sufficient for their intended purposes. However, there is a need in the art for an improved sheath construction, at least to decrease resultant suction effects during insertion. The subject invention provides a solution to this need.

SUMMARY OF THE INVENTION

A medical device includes an elongated tubular body having opposed proximal end and distal end portions and defining a longitudinal axis. The elongated tubular body includes an interior lumen extending therethrough. An inner surface of the interior lumen includes at least one channel therein configured to provide pressure relief for movement of a medical devise passing through the interior lumen.

The at least one channel can extend parallel to the longitudinal axis. The channel can extend between the proximal end and the distal end portions, can extend to either a proximal end opening of the interior lumen or a distal end opening of the interior lumen, and need not extend to either the proximal end opening of the interior lumen or to the distal end opening of the interior lumen.

The medical device can also include a pull wire lumen embedded within a wall of the tubular body. An outlet of the pull wire lumen into the interior lumen can be located longitudinally beyond a proximal end of the at least one depression and a distal end of the at least one depression. The pull wire lumen can be in fluid communication with a pull-wire port.

The tubular body can include an inner sheath wall and an outer layer. The inner sheath wall can include a lubricious material. The outer layer can include biocompatible polymers and a stainless steel braid or coil, where the steel braid or coil is embedded between the inner sheath wall and the outer layer. The inner sheath wall can include the at least one depression on an inner surface thereof. The outer layer can include a smooth outer surface defining the outer surface of the tubular body.

The depression can follow a straight line extending parallel to the longitudinal axis. It is also conceived that the at least one depression can include multiple isolated depressions or sections. The depression can include multiple depths and the channel can have a variable width as a function of position along the longitudinal axis.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF PREFERRED EMBODIMENTS

Figure 1:
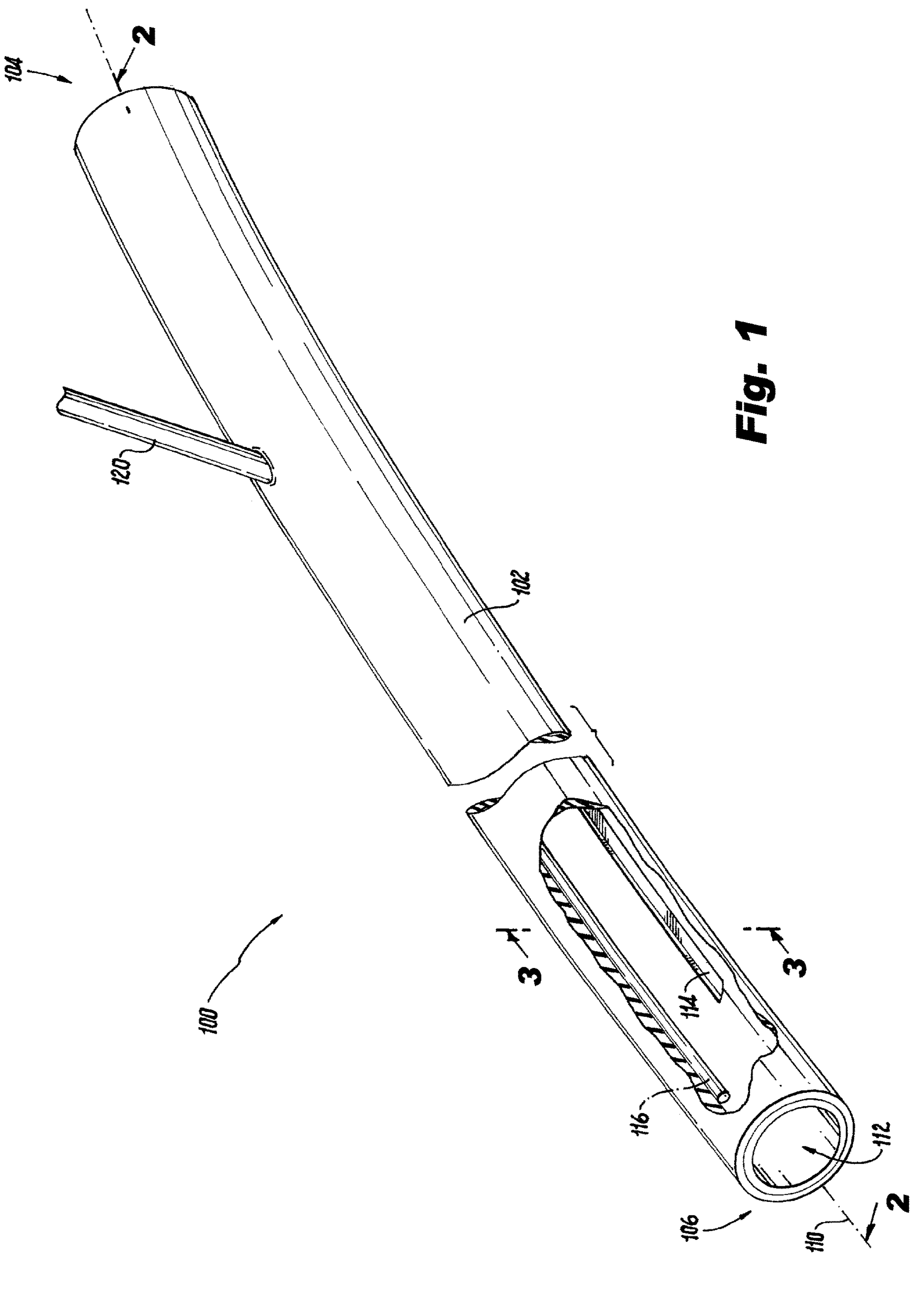
FIG. 1 is a perspective view of a sheath according to the disclosure.

Reference will now be made to the drawings wherein like reference numerals identify similar structural features or aspects of the subject invention. For purposes of explanation and illustration, and not limitation, a partial view of an exemplary embodiment of an implantable sheath in accordance with the invention is shown in FIG. 1 and is designated generally by reference character 100. Other embodiments of the sheath in accordance with the invention, or aspects thereof, are provided in FIGS. 2-3, as will be described.

FIG. 1 shows an implantable sheath 100. The sheath 100 includes an elongated tubular body 102 having an open proximal end 104 and an open distal end 106. The distal end 106 is inserted into the body. The sheath 100 can include either a straight tip at the distal end 106, a tip with a fixed curve of certain shape depending on the desired target location, or a deflectable tip version, allowing easy navigation and maneuverability throughout the vascular system. The proximal end 104 can be used with a hemostatic valve, allowing a user to introduce other devices into the sheath 100 through the hemostatic valve. Examples of such hemostatic valves are disclosed in U.S. Pat. No. 7,192,433 to Osypka, U.S. Pat. No. 9,572,957 to Osypka, and U.S. Pat. No. 8,137,317 to Osypka, the disclosures of which are incorporated herein by reference in their entireties.

Referring further to FIG. 1, the sheath 100 is elongated along longitudinal axis 110. The tubular body 102 includes an interior lumen 112 extending from the proximal end 104 to the distal end 106. The interior lumen 112 is intended to accept stents or artificial aortic valves, or therapies such as electrophysiology catheters, balloon catheters or other applications to the desired treatment location inside the heart or vascular system. Since these devices can obstruct the inner surface of the interior lumen 112, thereby possibly resulting in a suction effect, e.g., from the device passing through the interior lumen 112 acting like a piston, the inner surface of the interior lumen 112 includes at least one depression or channel 114 to provide a pressure release by-pass around the device when the interior lumen is blocked by a delivery device.

Figure 2:
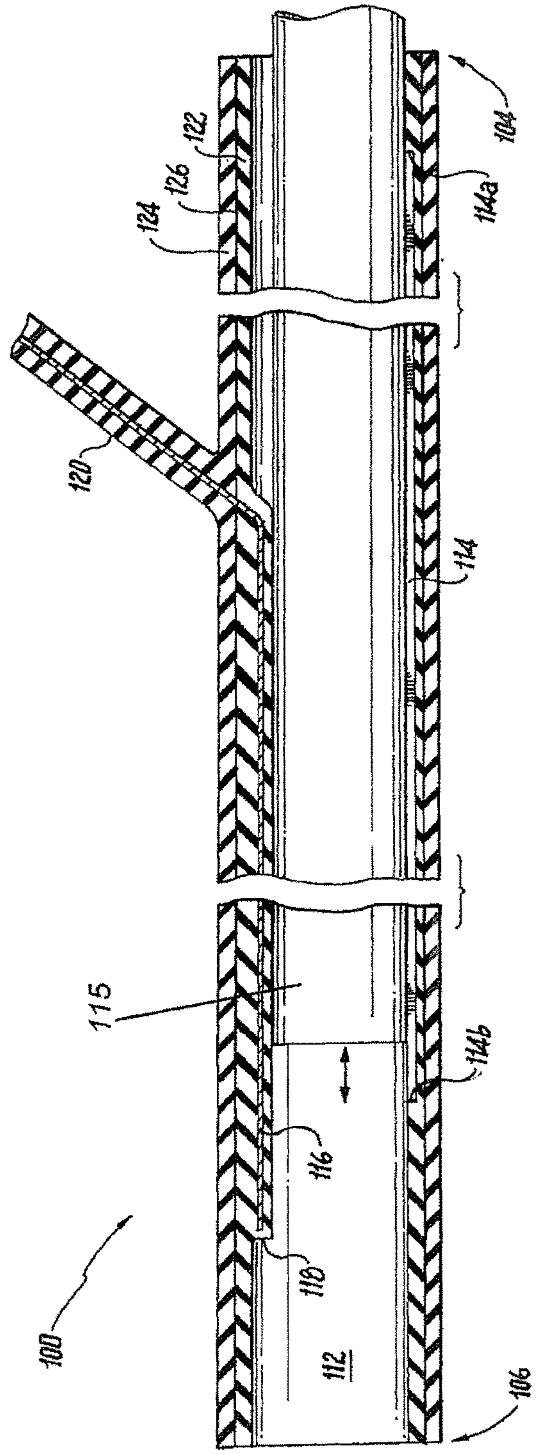
FIG. 2 is a cross-sectional side elevation view of the sheath of FIG. 1, showing the interior of the sheath.

Referring now to FIG. 2, a cross section of the sheath 100 is shown. The channel 114 is shown extending along the longitudinal axis 110. The channel 114 extends part of the way from the proximal end 104 and to the distal end 106, not fully reaching either end 104 or 106. One benefit of the channel 114 not extending all the way to the ends 104, 106 is that the channel 114 can provide a leak path for fluids, e.g., liquid or insufflation gas, to flow out of the body into the operating room. This arrangement is an important aspect for moving items 115 within lumen 112. For example, if a balloon is pulled back into the inner diameter of the catheter, it will cause a buildup of pressure inside the inner diameters of the catheter's proximal end until the balloon reaches the channel 114 to vent that pressure out the distal tip inside the body.

Referring further to FIG. 2, a wire lumen 116, with port 120, is also placed within the tubular body 102. The wire lumen 116 is located within the interior of the interior lumen 112, opposite the channel 114. An outlet 118 of the wire lumen 116 into the interior lumen 112 is not located between a proximal **114*a* and distal ends 114*b* of the channel 114. The outlet 118 is located longitudinally beyond the proximal end 114*a* and the distal end 114*b* of the channel 114**.

The sheath 100 is made up of an inner layer 122 and an outer layer 124. The inner layer 122 includes an inner sheath made up of partially a lubricious material, such as such as PTFE, FEP or Nylon, allowing the introduced devices 115 to be moved and pushed easily through the interior lumen 112, while the outer layer 124 includes biocompatible polymers, such as such as Nylons, PEBAX, and polyurethanes of various durometers. A reinforcing steel braid or coil 126 is embedded between the inner sheath wall 122 and the outer layer 124. The channel 114 is defined within the inner layer 122, while the outer layer 124 includes a smooth inner surface and a smooth outer surface.

Figure 3A:
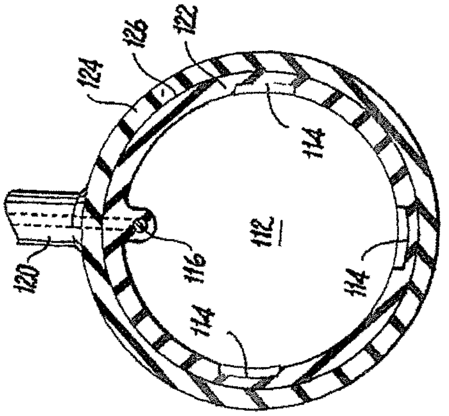
FIG. 3A is a cross-sectional front view of the sheath of FIG. 1, showing the sheath 100 having multiple channels 114 arranged circumferentially within the inner lumen 112.
Figure 3:
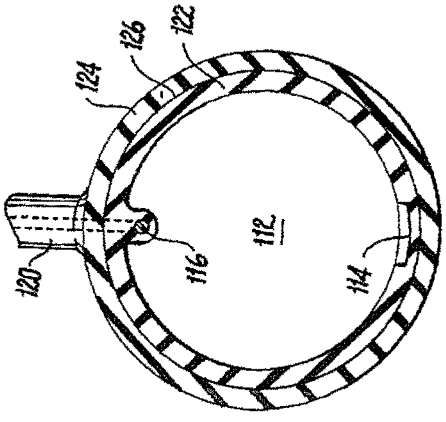
FIG. 3 is a cross-sectional front view of the sheath of FIG. 1, showing a depth of a pressure relief channel.

FIGS. 2 and 3 show the channel 114 extending along a straight line parallel to the longitudinal axis 110. Although a single depth as a function of location along the longitudinal axis 110 is depicted for channel 114, the channel 114 can include multiple depths or a variable depth as a function of position along the longitudinal axis 110. Similarly, although a constant circumferential width as a function of position along the longitudinal axis 110 is shown for the channel 114, the channel 114 can include a variable width, that widens or narrows depending on location along the longitudinal axis 110. The sheath 100 can also include more channels circumferentially separated from the channel 114. The channel 114 can also be discontinuous having multiple sections. The sheath 100 can include multiple channels 114 arranged circumferentially within the inner lumen 112. The channel 114 or channels can have various shapes including circular and elongated, and channels can be arranged in various patterns, including staggered and helical with respect to each other.

The methods and systems of the present disclosure, as described above and shown in the drawings, provide for an improved sheath, having the ability to relieve pressure build up from blockage and suction effects as devices traverse the inner lumen. While the apparatus and methods of the subject disclosure have been shown and described with reference to embodiments, those skilled in the art will readily appreciate that changes and/or modifications may be made thereto without departing from the spirit and score of the subject disclosure.

What is claimed is:

1. A medical device, comprising:

a) an elongated tubular body comprising an inner surface defining an interior lumen extending along a longitudinal axis to a proximal open end spaced from a distal open end of the tubular body, wherein the tubular body has a thickness that extends from the inner surface to an outer surface thereof;

b) at least one longitudinal depression extending from the inner surface part-way into the thickness of the tubular body without extending to the outer surface of the tubular body, wherein the at least one longitudinal depression extends longitudinally to a longitudinal depression proximal end that is spaced distally from the proximal open end to a longitudinal depression distal end that is spaced proximally from the distal open end of the interior lumen; and c) a pull wire lumen embedded within the thickness of the tubular body.

2. The medical device of claim 1, wherein the at least one longitudinal depression in the inner surface of the tubular body is a channel that is aligned parallel to the longitudinal axis.

3. The medical device of claim 2, wherein the at least one longitudinal depression is configured to provide pressure relief to accommodate movement of a medical device passing through the interior lumen of the tubular body.

4. The medical device of claim 1, wherein the pull wire lumen within the thickness of the tubular body is opposite the at least one longitudinal depression.

5. The medical device of claim 1, wherein an inner outlet of the pull wire lumen extends into the interior lumen of the tubular body between either the proximal end of the at least one longitudinal depression and the proximal open end of the interior lumen or the distal end of the at least one longitudinal depression and the distal open end of the interior lumen.

6. The medical device of claim 1, wherein the pull wire lumen is in fluid communication with a pull-wire port that opens through the outer surface of the tubular body.

7. The medical device of claim 1, wherein the tubular body comprises an inner layer and an outer layer.

8. The medical device of claim 7, wherein the inner layer comprises a lubricious material.

9. The medical device of claim 7, wherein the outer layer includes at least one biocompatible polymer.

10. The medical device of claim 7, wherein a steel braid or coil is embedded between the inner and outer layers of the tubular body.

11. The device of claim 7, wherein the outer layer of the tubular body has a smooth outer surface.

12. The device of claim 1, wherein the at least one longitudinal depression is a straight-line longitudinal depression that extends along the inner surface of the tubular body, aligned parallel to the longitudinal axis of the interior lumen.

13. The device of claim 1, wherein the at least one longitudinal depression has multiple depths extending into the thickness of the tubular body.

14. The device of claim 1, wherein the at least one longitudinal depression in the inner surface of the tubular body has a variable circumferential width as a function of position along the longitudinal axis from the longitudinal depression proximal end to the longitudinal depression distal end.

15. The medical device of claim 1, wherein the at least one longitudinal depression includes multiple longitudinal depressions extending from the inner surface part-way into the thickness of the tubular body without extending to the outer surface of the tubular body, the multiple longitudinal depressions each extending longitudinally to a longitudinal depression proximal end that is spaced distally from the proximal open end to a longitudinal depression distal end that is spaced proximally from the distal open end of the interior lumen, and wherein the multiple longitudinal depressions are isolated from each other in the tubular body.

16. A device, comprising:

a) a tubular body comprising an inner surface defining an interior lumen extending along a longitudinal axis to a proximal open end spaced from a distal open end, wherein the tubular body has a thickness that extends from the inner surface to an outer surface thereof;

b) an elongated channel extending from the inner surface part-way into the thickness of the tubular body without extending to the outer surface of the tubular body, wherein the elongated channel extends longitudinally to an elongated channel proximal end that is spaced distally from the proximal open end to an elongated channel distal end that is spaced proximally from the distal open end of the interior lumen; and c) a pull wire lumen within the tubular body, opposite the at least one longitudinal depression, wherein an inner outlet of the pull wire lumen extends into the interior lumen and is located longitudinally between either the proximal end of the at least one elongated channel and the proximal open end of the interior lumen or the distal end of the at least one elongated channel and the distal open end of the interior lumen, and wherein the pull wire lumen is in fluid communication with a pull-wire port that opens through the outer surface of the tubular body.

17. The device of claim 16, wherein a lubricious material portion of the tubular body includes the at least one elongated channel.

* * * * *